US010772609B2

(12) United States Patent
Chen et al.

(10) Patent No.: US 10,772,609 B2
(45) Date of Patent: Sep. 15, 2020

(54) ULTRASONIC IMAGING PROCESSING METHOD AND SYSTEM BASED ON RF DATA

(71) Applicant: Vinno Technology (Suzhou) Co., Ltd., Suzhou (CN)

(72) Inventors: Huiren Chen, Suzhou (CN); Tao Ling, Suzhou (CN); Jianjun Guo, Suzhou (CN); Dajun Yin, Suzhou (CN); Shui Xi, Suzhou (CN)

(73) Assignee: VINNO TECHNOLOGY (SUZHOU) CO., LTD., Suzhou (CN)

( * ) Notice: Subject to any disclaimer, the term of this patent is extended or adjusted under 35 U.S.C. 154(b) by 1082 days.

(21) Appl. No.: 14/851,647

(22) Filed: Sep. 11, 2015

(65) Prior Publication Data
US 2015/0374341 A1 Dec. 31, 2015

Related U.S. Application Data

(63) Continuation of application No. PCT/CN2015/072564, filed on Feb. 9, 2015.

(30) Foreign Application Priority Data

Feb. 20, 2014 (CN) .......................... 2014 1 0057108
Jan. 22, 2015 (CN) .......................... 2015 1 0033038

(51) Int. Cl.
*A61B 8/08* (2006.01)
*G01S 7/52* (2006.01)
(Continued)

(52) U.S. Cl.
CPC ........ *A61B 8/5207* (2013.01); *G01S 7/52077* (2013.01); *G01S 15/8977* (2013.01);
(Continued)

(58) Field of Classification Search
CPC .......... A61B 8/5207; A61B 8/00; G01S 7/00; G01S 15/00
See application file for complete search history.

(56) References Cited

U.S. PATENT DOCUMENTS 5,474,070 A * 12/1995 Ophir .................. A61B 5/0048
600/437
6,716,171 B1 4/2004 Brock-Fisher
(Continued)

FOREIGN PATENT DOCUMENTS

CN 1915175 A 2/2007
CN 101305923 A 11/2008
(Continued)

OTHER PUBLICATIONS

Pesavento, Andreas, et al. "A time-efficient and accurate strain estimation concept for ultrasonic elastography using iterative phase zero estimation." IEEE transactions on ultrasonics, ferroelectrics, and frequency control 46.5 (1999): 1057-1067 (Year: 1999).*

*Primary Examiner* — Pascal M Bui Pho
*Assistant Examiner* — Sean D Mattson
(74) *Attorney, Agent, or Firm* — Seed IP Law Group LLP

(57) ABSTRACT

An ultrasonic imaging processing method based on RF data includes the following steps: S1, receiving echo signals which are obtained by sending ultrasound signals; S2, beamforming the echo signals; S3, obtaining the RF data of the echo signals; and S4, directly conducting an ultrasonic imaging process based on the obtained RF data in order to obtain a target image. The ultrasonic imaging processing method and system based on the RF data according to the present application directly conduct ultrasonic imaging treatment based on the obtained RF data of the echo signals in order to obtain the target image.

10 Claims, 10 Drawing Sheets

(51) Int. Cl.
*G01S 15/89* (2006.01)
*A61B 8/14* (2006.01)

(52) U.S. Cl.
CPC .......... *A61B 8/14* (2013.01); *A61B 8/485* (2013.01); *A61B 8/488* (2013.01); *A61B 8/5269* (2013.01)

(56) References Cited

U.S. PATENT DOCUMENTS

| | | | |
|---|---|---|---|
| 8,951,196 B2 | 2/2015 | Itoh | |
| 2002/0002333 A1* | 1/2002 | Angelsen | G01S 7/52038 600/443 |
| 2007/0038101 A1* | 2/2007 | Yoon | A61B 8/0833 600/443 |
| 2008/0119732 A1* | 5/2008 | Hiltawsky | A61B 8/08 600/438 |
| 2009/0141957 A1* | 6/2009 | Yen | G01S 7/52047 382/131 |
| 2010/0113926 A1* | 5/2010 | Rigby | A61B 8/06 600/437 |
| 2012/0143057 A1* | 6/2012 | Itoh | A61B 8/488 600/441 |
| 2013/0046175 A1* | 2/2013 | Sumi | A61B 8/08 600/431 |

FOREIGN PATENT DOCUMENTS

| | | |
|---|---|---|
| CN | 101366642 A | 2/2009 |
| CN | 102469985 A | 5/2012 |
| CN | 103454640 A | 12/2013 |
| CN | 103815933 A | 5/2014 |
| WO | 2009/144717 A2 | 12/2009 |

\* cited by examiner

ULTRASONIC IMAGING PROCESSING METHOD AND SYSTEM BASED ON RF DATA

This application claims the benefit of priority to Chinese Patent Application No. 201410057108.4 titled "ULTRASONIC IMAGING PROCESSING METHOD AND SYSTEM BASED ON RF DATA", filed with the Chinese State Intellectual Property Office on Feb. 20, 2014, and also claims the benefit of priority to Chinese Patent Application No. 201510033038.3 titled "TIME DELAY ESTIMATION METHOD AND SYSTEM OF ULTRASONIC SIGNALS", filed with the Chinese State Intellectual Property Office on Jan. 22, 2015.

BACKGROUND

TECHNICAL FIELD

1. Technical Field

The present application relates to a field of ultrasound diagnostic imaging, more particularly to an ultrasonic imaging processing method and an ultrasonic imaging processing system based on RF (radio frequency) data.

2. Description of the Related Art

With the development of related fields such as electronics, computers and material science, the function of ultrasound diagnostic apparatus has been greatly improved in recent years. At the same time, medical ultrasound diagnosis technology occurred several revolutionary leaps. Now, it has become a preferred method for various clinical disease diagnosis and a necessary tool of ultrasound diagnosis during ultrasound imaging. Correspondingly, B mode ultrasound imaging, CF mode ultrasound imaging and PW mode ultrasound imaging etc., are those most basic and most widely used technologies in ultrasound imaging systems. There are many clinical applications of various modes of ultrasound imaging, e.g., to monitor the fetus status in obstetrics, or for valvular heart disease diagnosis in internal medicine. Ultrasound imaging technology has been widely studied and applied globally. But because of constant update of ultrasound devices, application demands of ultrasonic inspection and clinical diagnoses etc., continuously increased. As a result, new content and new technologies emerge endlessly. The existing study is unable to meet the demand for ultrasound imaging applications.

Traditional modes of ultrasound imaging include a front-end processing, a middle processing and a back-end processing, wherein the front-end processing is used to get focused RF signals, the middle processing is used to get the baseband signals and the back-end processing is used to display signals after being scanned and converted. Since the back-end processing technology is only in a preliminary development stage, and also considering the computer processing capacity, in the existing technology, the echo signals are divided into two I/Q signals in the middle processing, and the echo signals are treated by desampling and dropping bit in order to match the computer processing capacity. As a result, the whole processing needs large hardware support, especially for the middle processing, it usually needs dedicated chip or digital signal processor, which makes the processing chain extremely complex. For example, FIG. 1 shows a flowchart of an existing processing method in the ultrasound imaging technology. The method includes the following steps: P1, receiving echo signals which are obtained by sending ultrasound signals; P2, beamforming the echo signals; P3, obtaining the RF data of the echo signals; P4, orthogonally demodulating or Hibert transforming the RF data in order to divide the RF data into two I/O orthogonal signals; P5, treating the two I/O orthogonal signals obtained from the step P4 via baseband filtering or low-pass filtering in order to desample and drop bit of the two I/O orthogonal signals; P6, treating the two I/O orthogonal signals processed after the step P5 via ultrasound imaging in order to obtain a target image.

SUMMARY

In order to facilitate addressing the above problems, an embodiment of the present application provides an ultrasonic imaging processing method and an ultrasonic imaging processing system based on RF data, with simple structure and without loss of data information.

An embodiment comprises an ultrasonic imaging processing method based on RF data. The method comprises the following steps:

S1, receiving echo signals which are obtained by sending ultrasound signals;

S2, beamforming the echo signals;

S3, obtaining RF data of the echo signals;

S4, directly conducting an ultrasonic imaging process based on the obtained RF data in order to obtain a target image.

An embodiment comprises an ultrasonic imaging processing system based on RF data. The system comprises:

an ultrasonic probe module for sending and receiving ultrasound signals;

an ultrasound echo receiving module for receiving echo signals obtained by sending the ultrasound signals;

a beam synthesis module for beamforming the echo signals;

a RF data transmitting and storage module for getting the RF data of the echo signals;

an image processing module for directly conducting ultrasonic imaging based on the obtained RF data in order to obtain the target image.

Embodiments of the ultrasonic imaging processing method and the ultrasonic imaging processing system based on RF data of the present application are capable of directly conducting ultrasonic imaging based on the obtained RF data in order to obtain the target image, after getting the RF data of the echo signals. Compared with the existing technology, the system structure is simple, but without loss of data information, which facilitates improving real-time performance and image quality of ultrasonic diagnose, making diagnostic information and axial resolution in more detail and clearer, and also lowering the cost of manufacture and usage.

DETAILED DESCRIPTION

Detailed description of the present application will be depicted in combination with embodiments shown in figures. It should be noted that the present application should not be restricted to the embodiments, and modifications of structure, method and function to those of ordinary skill in the art according to the embodiments are all included within the protection scope of the present application.

Figure 2:
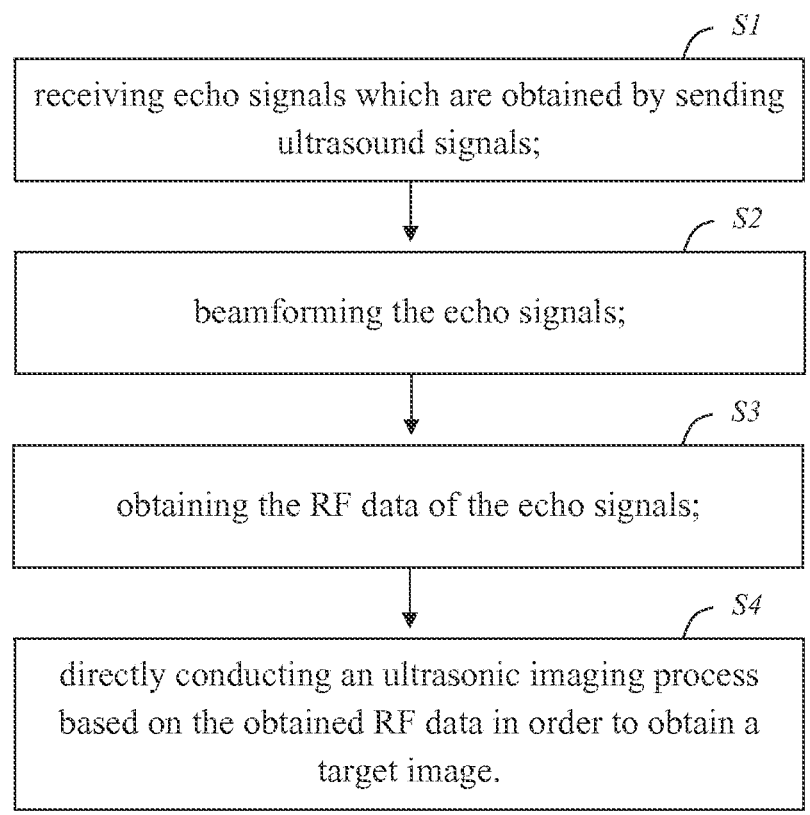
FIG. 2 is a flowchart of an ultrasonic imaging processing method based on RF data in accordance with a first embodiment of the present application.

Referring to FIG. 2 which is a flowchart of an ultrasonic imaging processing method based on RF data in accordance with a first embodiment of the present application. Correspondingly, the method includes the following steps:

S1, receiving echo signals which are obtained by sending ultrasound signals;

S2, beamforming the echo signals;

S3, obtaining RF data of the echo signals;

S4, directly conducting an ultrasonic imaging process based on the obtained RF data in order to obtain a target image.

Figure 1:
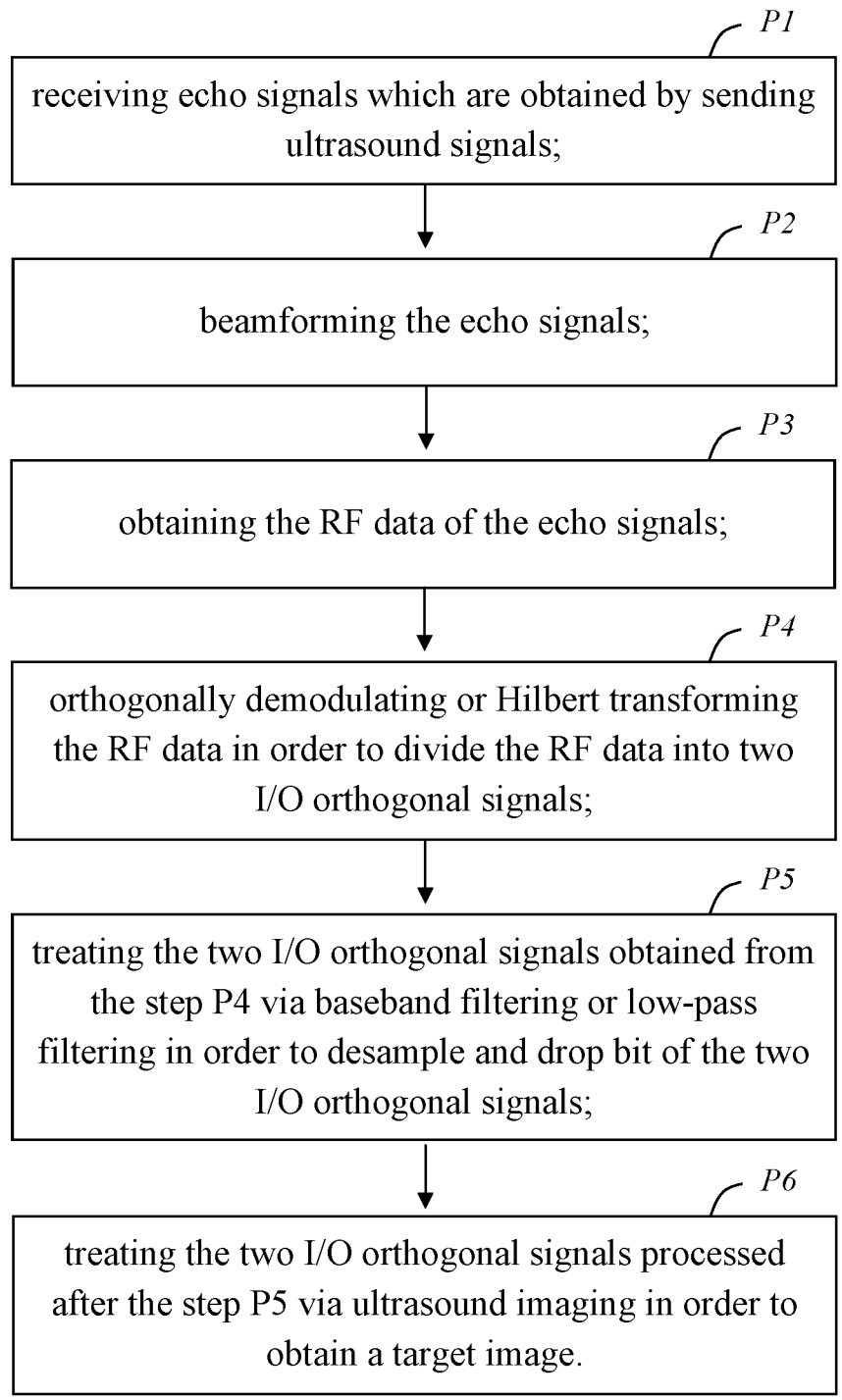
FIG. 1 is a flowchart of an existing ultrasound imaging processing method.

In the above description of the ultrasonic imaging processing method based on RF data, the steps S1, S2 and S3 are similar to the existing technology shown in FIG. 1, detailed description thereof will be omitted herein. The difference between the present application and the existing technology is that the present application is capable of directly conducting ultrasonic imaging based on the obtained RF data in order to obtain the target image. Even though the system structure for achieving the method is simple, there is no loss of data information in an embodiment. Besides, real-time performance and image quality of ultrasonic diagnose using the ultrasonic imaging processing method and the ultrasonic imaging processing system are improved in an embodiment, which facilitates making diagnostic information and axial resolution in more detail and clearer, and also facilitates lowering the cost of manufacture and usage at the same time.

The "RF" of the RF data is an abbreviation of radio frequency.

Detailed example embodiments of the present application will be depicted in more detail hereinafter.

Based on the obtained RF data, the step S4 specifically includes adopting B mode processing, CF mode processing, PW mode processing and EI mode processing in order to obtain the target image.

The "CF" of the CF mode processing is an abbreviation of color flow which means blood flow imaging in Chinese. The "PW" of the PW mode processing is an abbreviation of pulsed wave doppler. The "EI" of the EI mode processing is an abbreviation of elastography which means tissue elasticity imaging in Chinese.

In an embodiment of the present application, adopting B mode processing to obtain the target image includes conducting gray scale map imaging of the obtained RF data. Accordingly, there are two ways to use the B mode to obtain the target image.

The first way: assuming the RF signal data output by the beam synthesis is I, the absolute value of the RF signal data |I| is used for gray map imaging.

The second way: assuming the RF signal data output by the beam synthesis is I and then constructing I' using the following formulas:

$$I = A \times \text{Cos } \omega t,$$

$$I' = A \times \text{Cos}(\omega t + \phi),$$

Then, we can achieve the following formulas:

$$\begin{cases} I + I' = 2A\text{Cos}\left(\omega t + \frac{\phi}{2}\right)\text{Cos}\frac{\phi}{2} \\ I - I' = 2A\text{Sin}\left(\omega t + \frac{\phi}{2}\right)\text{Sin}\frac{\phi}{2} \end{cases}$$

And then, we can achieve the following formula from the above one:

$$tg\left(\omega t + \frac{\phi}{2}\right) = \frac{I - I'}{I + I'} ctg\left(\frac{\phi}{2}\right),$$

In combination with the formula:

$$tg\left(\omega t + \frac{\phi}{2}\right) = \frac{tg(\omega t) + tg(\phi/2)}{1 - tg(\omega t)tg(\phi/2)},$$

we can achieve tg (ωt). Under this condition, the mode |A| of the RF signal data will be used for gray map imaging using the following formula:

$$|A| = |I/\text{Cos } \omega t|.$$

According to an embodiment of the present application, adopting CF mode processing to obtain the target image includes adopting ButterflySearch algorithm or CrossCorrelation algorithm directly conducting ultrasonic imaging based on the obtained RF data in order to obtain the target image.

The ButterflySearch algorithm of the CF mode processing is carried out by searching along dimensions of depth and time of the objective reflection ultrasonic signals. The slope of butter line with maximum matching rate is corresponding to the target axial movement speed.

The CrossCorrelation algorithm applied in the CF mode processing is achieved by cross-correlation operating the objective reflection ultrasonic signals along a depth direction. The peak position of the cross-correlation coefficient is corresponding to shift caused by movement. Then the target axial movement speed can be calculated. This algorithm is mainly based on the signal time shift generated by the target movement. In actual calculation, a cross-correlation operation will be done between two adjacent RF data within a sampling volume in order to calculate a speed, and then the total calculated speeds are averaged to get a final speed for the sampling volume.

In an embodiment of the present application, an improved CrossCorrelation algorithm is adopted to directly conducting ultrasonic imaging based on the obtained RF data in order to obtain the target image.

In detail, traditional CrossCorrelation algorithm can only obtain time shift with integer times of the sampling interval, which requires interpolation in order to achieve the precise shift. There are two kinds of interpolation methods. The first method is interpolation on RF signal in order to upsampling. But interpolation cannot meet the real-time requirement because of high computation complexity. The second method is parabolic, sine or cosine interpolation on cross-correlation coefficient. Although this method can meet real-time requirements, it is necessary to ensure that true cross-correlation peak is indeed contained in the interpolation curve, which is easily matched to an incorrect peak.

In an embodiment of the present application, if the CrossCorrelation algorithm is adopted to directly conduct ultrasonic imaging based on the obtained RF data in order to obtain the target image, based on the conventional Cross-Correlation algorithm, a limited searching scope will be defined through prior value in order to avoid matching error peak cross-correlation coefficient. This will simplify the computation complexity of CrossCorrelation algorithm, and facilitate meeting the real-time requirements.

Time shift (or displacement) of a traditional RF signal is continuous along the axial direction and the lateral direction. So, the prior value is calculated as the shift of previous point which is in line with the current point, or the shift of a same location of an adjacent line corresponding to the current point. For example, if the shift of previous point in the same line is 2, then the shift of the current point is around 2, and cross-correlation search scope can be set between [1, 3].

In an embodiment of the present application, a CrossCorrelation algorithm can be adopted to directly conduct ultrasonic imaging based on the obtained RF data in order to obtain the target image. Besides, it is also feasible to combine the CrossCorrelation algorithm with AutoCorrelation algorithm to directly conduct ultrasonic imaging based on the obtained RF data in order to obtain the target image.

First, a rough shift value can be calculated by using the CrossCorrelation algorithm. The RF signal can be intercepted based on the rough shift value. Then, a precise shift value can be calculated by using the AutoCorrelation algorithm. The final accurate shift value can be achieved by adding these two shift values.

In combination with the above description, before adopting the CrossCorrelation algorithm, by limiting the cross-correlation search scope through prior values, the shift value of previous point or adjacent point can be directly used as rough shift value of current point. Then, the AutoCorrelation algorithm is used to calculate a precise shift value. By using this method, it is possible to minimize the calculation complexity of the CrossCorrelation algorithm, and avoid aliasing of precise shift value calculated by AutoCorrelation algorithm.

In the process of calculating the precise shift value by using the AutoCorrelation algorithm, it only needs temporarily Hilbert demodulation of the RF signal. Such process can be implemented at the algorithm layer, which simplifies the system structure while avoiding data loss.

In an embodiment of the present application, adopting PW mode processing to obtain the target image includes adopting a ButterflySearch algorithm or CrossCorrelation algorithm to directly conduct ultrasonic imaging based on the obtained RF data in order to obtain the target image.

The ButterflySearch algorithm for achieving the target image of the PW mode processing is to obtain data of each rate component along a depth direction of the RF signal in the sampling box and also along a slope of the velocity. The size of the corresponding data is then calculated for spectrum display.

In an embodiment of the present application, the step S4 also includes adopting EI mode processing to obtain the target image based on the obtained RF data.

It is noted that, in existing technologies, there are multiple ways to obtain a target image by adopting the EI mode, among which it is particularly noticeable as to time delay estimation in the process of obtaining the target image of the EI mode.

Currently, there are a lot of time delay estimation methods commonly used in the EI mode processing, including CrossCorrelation method, AutoCorrelation method, a method combining the CrossCorrelation method and the AutoCorrelation method, zero-phase iterative method, maximum likelihood method, and frequency domain processing method, etc. The methods mentioned above have their own advantages and disadvantages.

Among them, the most classic time delay estimation algorithm is the CrossCorrelation method. The time delay is determined by calculating the cross-correlation coefficient between adjacent ultrasonic RF signals. It is the place where the cross-correlation coefficient has the maximum value corresponds to the time delay of the signals. In using the CrossCorrelation method, it is only feasible to get the integer multiple time delay of the sampling period through the place where the cross-correlation coefficient has the maximum value, because the ultrasonic signals have limited sample rate. However, in some applications (such as shear wave elasticity imaging or temperature monitoring), the time delay of the ultrasonic signals is even less than one sampling period. In order to get sub-sample time delay estimation, it is typical in the CrossCorrelation method by using interpolation of the ultrasonic RF signals or CrossCorrelation coefficients. It will tend to much additional calculation by using interpolation of the ultrasonic RF signals. So, it is necessary to exhaustively search the signals in a given range in the CrossCorrelation method, which is an extremely big calculation load. And, when the signal delay is less than one sampling period, the sub-sample time delay estimation obtained by the interpolation method may have large errors.

Further, in order to reduce the calculation load of the CrossCorrelation algorithm, some simplified methods such as sum of absolute difference (SAD) and sum of squared differences (SSD) have been proposed. Although these methods have small calculation load, they are less accurate than the CrossCorrelation method.

Further, the AutoCorrelation method is classic delay or phase-shift estimation algorithm which has been widely used in the field of ultrasonic doppler, usually calculating in the complex field. Comparing with the interpolation operation of the CrossCorrelation method, the AutoCorrelation method does not need exhaustive search so that the calculation load is small, and it can get the precise sub-sample time delay estimation. However, the flaw of the AutoCorrelation method is, when the signal delay is large (greater than half period signal), it will cause phase winding, also called aliasing. In addition, for accuracy consideration, the AutoCorrelation method is more suitable to narrow-band signals rather than wide-band signals.

Further, when the AutoCorrelation method based on the parsing signal is used for time delay estimation of the ultrasound signal, the method firstly applies Hilbert change to the ultrasound RF signal in order to get plural domain parsing signal. Then AutoCorrelation operation takes place regarding the parsing signal in a given range. The maximum place of the model of the auto-correlation coefficient corresponds to integer time delay of the sampling period. And then, sub-sample time delay can be calculated using the phase of the maximum place of the auto-correlation coefficient and the phase of an adjacent front point or an adjacent rear point. The eventual time delay can be achieved by adding them. This method resolves the aliasing of the AutoCorrelation operation and is suitable for any bandwidth signal. But the method needs to process the plural domain parsing signal (including the real part and the imaginary part), and still requires exhaustive search of the signals within a certain range. As a result, the calculation load is greater than the CrossCorrelation method. The robust capability is not good because in order to get the precise sub-sample time delay, it is necessary to precisely calculate the integer time delay of the sampling period.

Further, regarding the method combining the CrossCorrelation method and the AutoCorrelation method applied for time delay estimation of ultrasonic signals, firstly, a "rough time delay" of the method is obtained via a cross-correlation operation, using signal half wavelength (half cycle) as a step. Then, the AutoCorrelation operation is adopted based on the signal reference point of the "rough time delay" in order to get a "precise time delay". Then the final time delay will be obtained by adding the "rough time delay" and the "precise time delay". This method greatly reduces the calculation load of the CrossCorrelation operation. At the same time, this method facilitates precise estimation of the sub-sample time delay by using AutoCorrelation operation. As a result, this method is a practical method. However, in actual application, an orthogonal base band signal is normally given a down-sampling, if step length of the CrossCorrelation operation is too big, a mutual related coefficient may miss the real peak and then generate a pseudo peak, which means that the value of the "rough time delay" could be totally wrong and may eventually led to singular value of delay estimation. In addition, ultrasound signal in human organization will constantly attenuate. Signal center frequency $f_0$ will actually get gradually reduced with depth going deeply, which will also result in estimation error of "precise time delay".

Further, regarding the zero phase iterative method for time delay estimation of ultrasonic signals, its principle is to get an initial phase by AutoCorrelation calculation of orthogonal base signal $S_r$ and $S_d$, and get a new $S'_d$ using interpolation method according to the $S_d$ according to the initial phase. Then a calculation between $S_d$ and $S'_d$ will be conducted to get the phase therebetween. Then, a new $S'_d$ will be obtained by using interpolation method according to the previously accumulated phase of $S_d$. The above iteration process will be repeated until the phase between $S_r$ and $S'_d$ tends to near zero, which is so called zero phase iterative method. It is possible to set maximum iteration time or phase threshold. When the iteration time reaches the maximum value or is less than the threshold value, the iterative process will be over. The final phase shift will be obtained by accumulating all the iteration phases. Zero phase iterative method solves the aliasing problem in AutoCorrelation method, but the method raises an error calculation when the signal central frequency f0 gets gradually reduced with depth going deeply.

In addition, some other time delay estimation methods of ultrasonic signals, such as maximum likelihood method and frequency domain processing method etc., which are rarely used in the prior art because of big defects. Detailed description of them is omitted herein.

Figure 6:
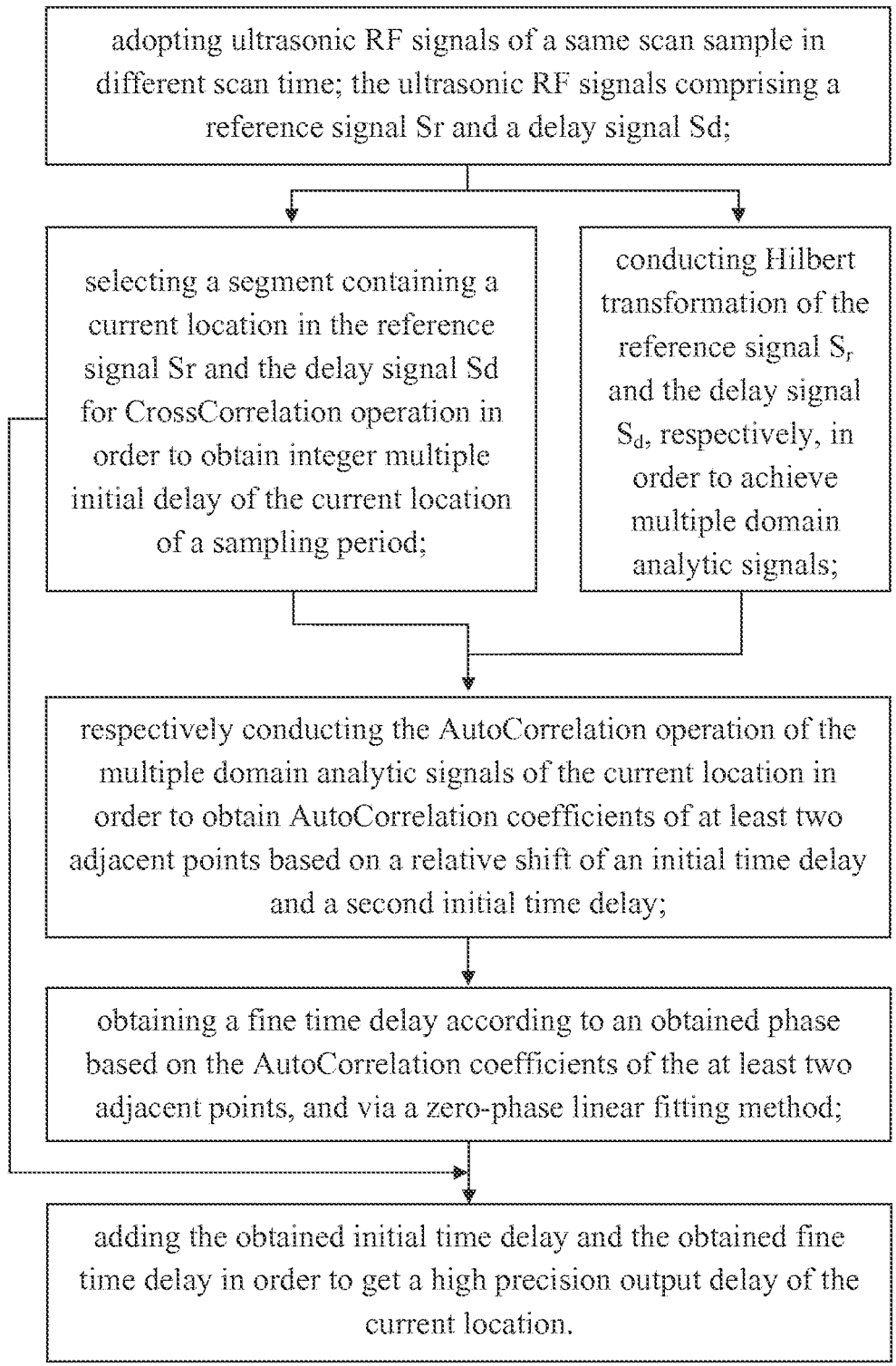
FIG. 6 is a flowchart of adopting EI mode processing based on RF data in order to obtain the target image.
Figure 7:
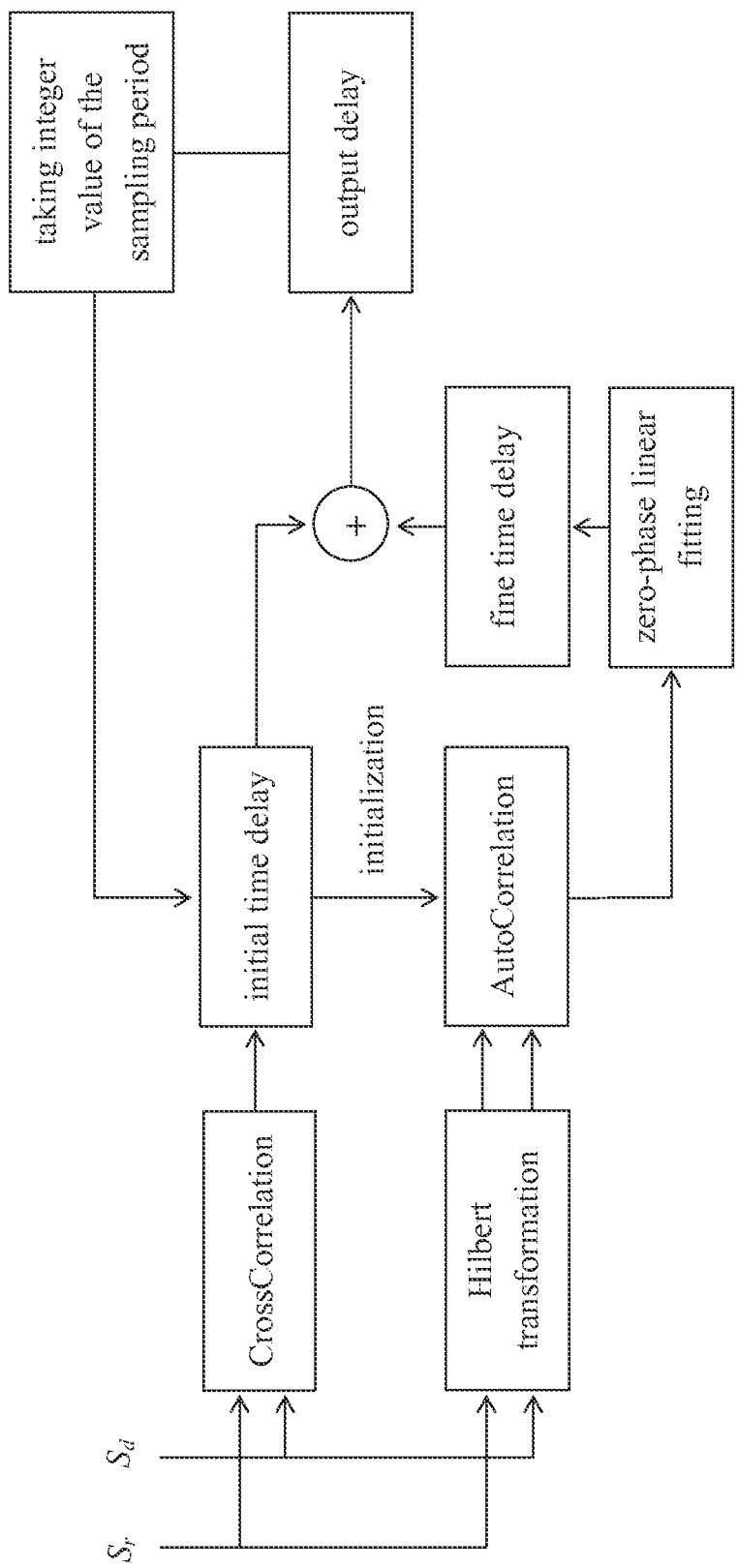
FIG. 7 is a simplified structure diagram of FIG. 6.

Referring to FIGS. 6 and 7, in an embodiment of the present application, the method adopting EI mode processing to achieve target image includes the following step:

obtaining ultrasonic RF signals of the same scan sample in different scan times. The ultrasonic RF signals include a reference signal $S_r$ and a delay signal $S_d$.

In the current embodiment, the ultrasonic RF signals are RF data.

The target image is obtained by directly proceeding based on the obtained RF data. So, it simplifies the time delay estimation method of ultrasonic signals while avoiding data information loss. As a result, real-time performance and image quality of ultrasonic diagnose appliance by using the proceeding method may be improved.

Further, in this embodiment, the method adopting EI mode processing to achieve target image includes selecting a section containing the current position of the reference signal $S_r$ and the delay signal $S_d$ for CrossCorrelation operation in order to get integer multiple initial delay of the current location sampling period.

It is understandable that, for easy calculation and low amount of calculation, a section containing the current position of the reference signal $S_r$ and the delay signal $S_d$ is usually selected for CrossCorrelation operation. Besides, in an embodiment of the present application, the selected section could be a signal having the current position as its center, which will not be described in detail herein.

In the present embodiment, after conducting the CrossCorrelation operation as to the section containing the current position of the reference signal $S_r$ and the delay signal $S_d$, the CrossCorrelation function will be expressed as follows:

$$R_{cc}(m, n, d) = \sum_{m'=-M}^{M} \sum_{n'=-N}^{N} S_r(m + m', n + n') S_d(m + m' + d, n + n')$$

Wherein, m represents signal axis location, n represents signal horizontal location. Value range of m' is between −M to M. Value range of n' is between −N to N. The range between −M and M represents 2M plus one points with the point (m, n) as a center, along the axis direction. The range between −N and N represents 2N plus one point with the point (m, n) as a center, along the horizontal direction. That is to say, the mutual window of the location (m, n) is [2M+1, 2N+1]. Wherein, d represents signal axial relative shift. $R_{cc}(m, n, d)$ represents a CrossCorrelation coefficient, when the signal is located at the location (m, n) and the axial relative shift is d. If the maximum search range d belongs to [−D, D], after calculating all the CrossCorrelation coefficients of the range, assuming the maximum location of the CrossCorrelation coefficient is $d_0$, the $d_0T_s$ is exactly the integer multiple initial delay of the current location sampling period.

In an embodiment of the present application, the method for obtaining integer multiple initial delay of the current location sampling period can also be applied to obtain integer multiple initial delay of the current location sampling period of adjacent locations, which will not be depicted in detail herein.

Normally, the CrossCorrelation operation only provides integer multiple initial delay of the current location sampling period and does not accompany the entire process. In order to avoid strange value of the integer multiple initial delay of the current location sampling period, usually CrossCorrelation operation is also applied to multiple adjacent locations in order to get integer multiple initial delay of the current location sampling period of the adjacent locations. Then, a filtering process is applied regarding the obtained multiple initial delay in order to get a middle value as the initial time delay of the current location.

Further, in the present embodiment, the method adopting EI mode processing to achieve target image includes obtaining multiple domain analytic signal of the reference signal $S_r$ and the delay signal $S_d$ by Hilbert transformation.

In the present embodiment, using the $CS_r$ and $CS_d$ to represent the multiple domain analytic signals obtained by Hilbert transformation of the reference signal $S_r$ and the delay signal $S_d$, respectively, the AutoCorrelation function will be expressed as follows:

$$R_{ac}(m, n, d) = \sum_{m'=-M}^{M} \sum_{n'=-N}^{N} CS_r(m + m', n + n') CS_d^*(m + m' + d, n + n')$$

Wherein, symbol * represents conjugate, m represents signal axis location, n represents signal horizontal location. Value range of m' is between −M to M. Value range of n' is between −N to N. The range between −M and M represents 2M plus one points with the point (m, n) as a center, along the axis direction. The range between −N and N represents 2N plus one point with the point (m, n) as a center, along the horizontal direction. That is to say, the mutual window of the location (m, n) is [2M+1, 2N+1]. Wherein, d represents signal axial relative shift. $R_{ac}(m, n, d)$ represents an AutoCorrelation coefficient, when the signal is located at the location (m, n) and the axial relative shift is d.

Since the center frequency of the ultrasonic signals is slowly changing with depth going deeply, phase of partial signal keeps linearity.

Further, in the present embodiment, the method adopting EI mode processing to achieve target image further includes conducting AutoCorrelation operation of the multiple domain analytic signal of the present location based on a relative shift between the initial time delay and a second initial time delay in order to achieve the AutoCorrelation coefficient of at least two adjacent points. The second initial time delay is a time delay which has an adjacent value of the initial time delay, and is achieved by retaking an integer multiple sampling cycle with respect to the initial time delay.

Considered the continuity in space of the ultrasound signal delay, each calculated output time delay of the current location can be used as an initial time delay of a next location (axial) or an adjacent location (horizontal). As a result, follow-up calculation process does not need to rely on the mutual related exhaustive search. It is only needed to calculate the AutoCorrelation coefficients of at least two points with respect to the initial time delay, which greatly reduces calculation load.

In the above example, the initial time delay of the determined location (m, n) is $d_0 T_s$. In the present embodiment, AutoCorrelation coefficients of the relative shift $d_0$ and at least two adjacent points will be calculated. Take three points for example, AutoCorrelation coefficients will be calculated in turn and obtained as [$R(m,n,d_0-1)$, $R(m,n,d_0)$, $R(m,n,d_0+1)$].

Further, in the present embodiment, the method adopting EI mode processing to achieve target image further includes obtaining a phase based on the AutoCorrelation coefficients of at least two adjacent points, and a fine time delay by using zero-phase linear fitting method.

Figure 8A:
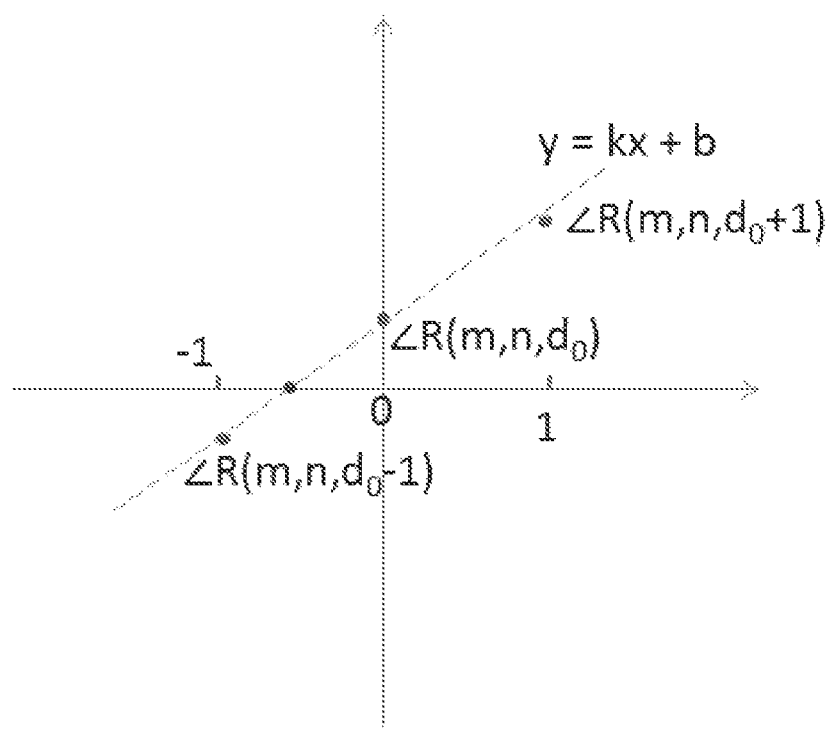
FIGS. 8A and 8B are zero-phase linear diagrams in the process of adopting EI mode processing based on RF data in order to obtain the target image of FIG. 6.
Figure 8B:
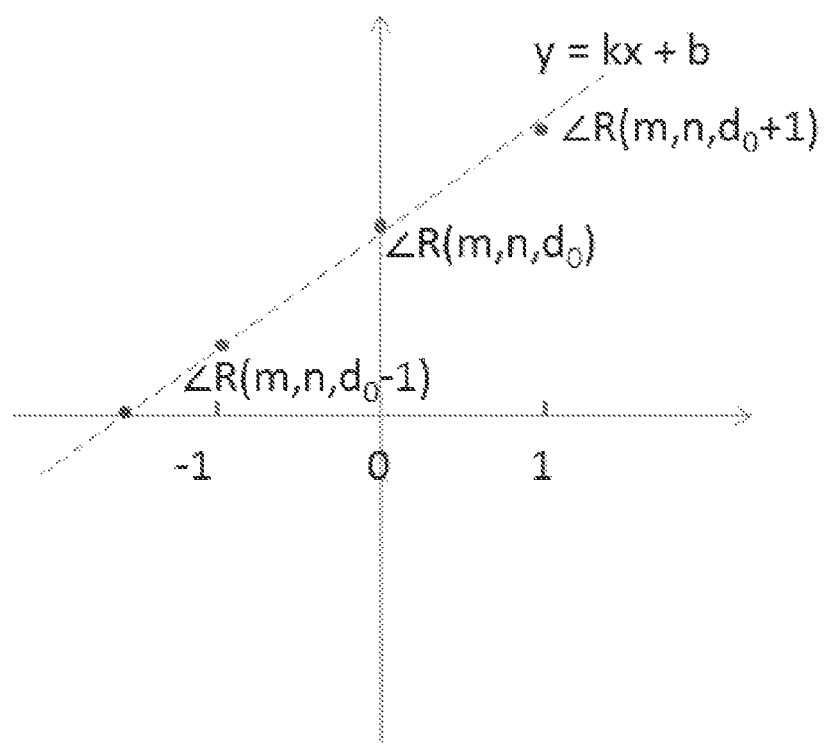

In an embodiment of the present application, referring to FIGS. 8A and 8B, the difference between the initial time delay and the actual time delay is less than one sampling period according to the zero-phase linear fitting shown in FIG. 8A. The difference between the initial time delay and the actual time delay is greater than one sampling period according to the zero-phase linear fitting shown in FIG. 8B.

Accordingly, the phase obtained based on the AutoCorrelation coefficients of at least two adjacent points, and the fine time delay obtained by using zero-phase linear fitting method specifically include:

calculating each phase according to the AutoCorrelation coefficients of at least two adjacent points; getting slope and intercept of the phases of the obtained at least two points by linear fitting operations; and taking the time delay corresponding to the fitted linear zero phase according to the calculated slope and the calculated intercept as the fine time delay.

Zero-phase linear fit ensures the accuracy of the sub sample delay so that the final time delay estimation precision is good. Specifically, based on phase linear characteristics of partial signal, it is possible to conduct linear fit of the above AutoCorrelation coefficients in order to obtain line y=kx+b. Wherein k represents the slope, b represents the intercept, the symbol < represents achieving phase angle which means <(x+jy)=arctan (y/x). As a result, the intersection of the line and the X axis represents the zero phase location, and the time delay corresponds to the intersection is $$-\frac{b}{kT_s}.$$

Further, the fine time delay is actually the time delay $$-\frac{b}{kT_s}.$$

Further, in the present embodiment, the method adopting EI mode processing to achieve target image further includes adding the obtained initial time delay and the obtained fine time delay in order to get a high precision output delay of the current location.

According to the above example, the high precision output delay of the current location is $$-\frac{b}{kT_s+d_0 T_s}.$$

It is understandable that in the present application, it is possible to use a least square method as a linear fit method, which will not be detailed herein.

Further, under normal circumstances, it is necessary to calculate time delays of all locations of a frame signal in an ultrasound scanning process. The frame signal usually includes multiple signals each of which includes time delays corresponding to multiple locations at different depths.

Further, in the present embodiment, the method adopting EI mode processing to achieve target image further includes taking integer value of the sampling period as an initial time delay of the next location based on the high precision output delay of the current location, and then calculating the time delay of the high precision output delay of the next location using the above method. The next location is a location corresponding to a next depth of a signal which is in the same column of the current signal, or the same depth of a signal of an adjacent column of the current signal.

Figure 9:
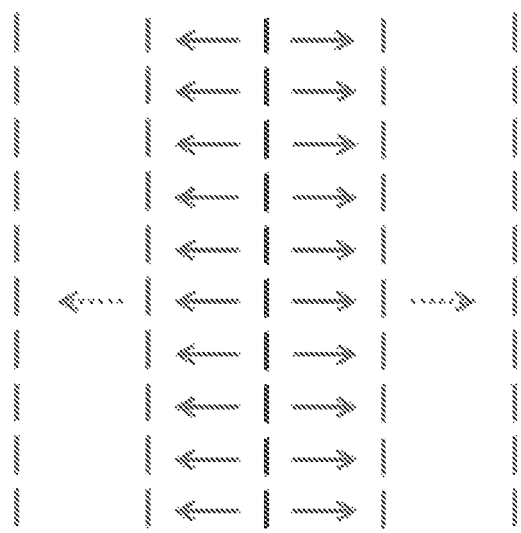
FIG. 9 is a schematic diagram showing initial delay of multiple places of a frame signal in the process of adopting EI mode processing based on RF data in order to obtain the target image of FIG. 6.

Referring to FIG. 9, in an embodiment of the present application that adopting EI mode processing method to achieve target image, the initial time delay of all locations of the column signal is obtained through CrossCorrelation operation. In order to remove strange values, a middle value filtering processing is further used to treat the initial time delay of all locations of the column signal. Then, high precision output delay of all the locations of the column signal will be calculated and obtained. As shown by the arrows of FIG. 9, the high precision output delay of the current location will be used as an initial time delay of a corresponding location of an adjacent signal. Following this rule in turn, calculations will be completed until both the left and the right reach the boundary.

Further, the high precision output delays of all the locations of the obtained frame signal are integrated in order to form an image or achieve a new image based on the image in subsequent processing. In a word, adopting the B mode proceeding, the CF mode proceeding, the PW proceeding and the EI mode processing to obtain the target image, in the process of directly calculating and searching the RF data, it directly conducts ultrasonic imaging based on the obtained RF data in order to obtain the target image. Comparing with existing technology, the present application obtains I/Q orthogonal signal based on the processing of the RF data, and generates the target image based on the I/Q orthogonal signal via ultrasound imaging processing. The sampling data obtained in such process is more accurate and the calculation result is more accurate as well. Besides, when using the EI mode processing to obtain target image, the EI mode has the advantages of low calculation load and excellent robustness capability, which has very high utility value.

Figure 3:
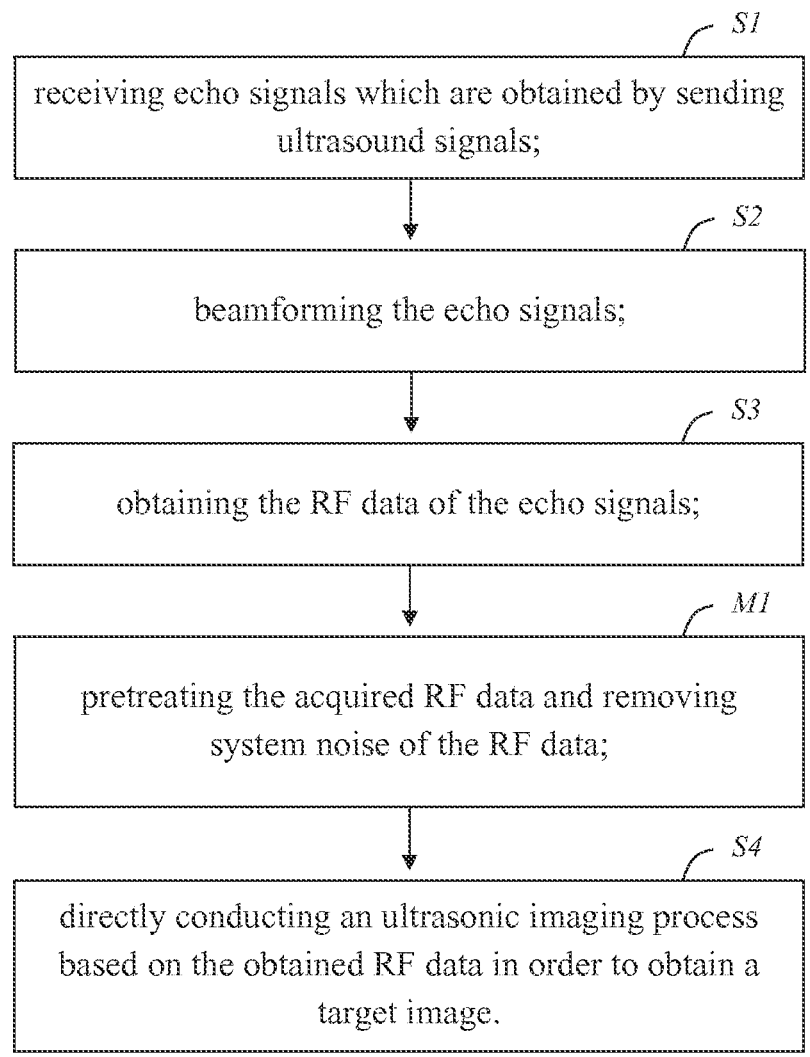
FIG. 3 is a flowchart of an ultrasonic imaging processing method based on RF data in accordance with a second embodiment of the present application.

Referring to FIG. 3, FIG. 3 shows a flowchart of an ultrasonic imaging processing method based on RF data in accordance with a second embodiment of the present application. Accordingly, the second embodiment of the present application is similar with the first embodiment, the main difference is that the method further comprises a following step after obtaining RF data of the echo signals shown in the step S3:

M1, pretreatment the acquired RF data and removal of system noise in the RF data.

Accordingly, there are a lot of ways to pretreat the acquired RF data and remove the system noise in the RF data. In an embodiment of the present application, the following method is adopted for removing the system noise in the RF data.

Accordingly, noise RF signal data $I_0$ is removed when the collection system is under a silent status. By assuming that the RF signal data of the ultrasonic echo in practical application is I, it is possible to remove the background noise by using I minus $I_0$.

Figure 4:
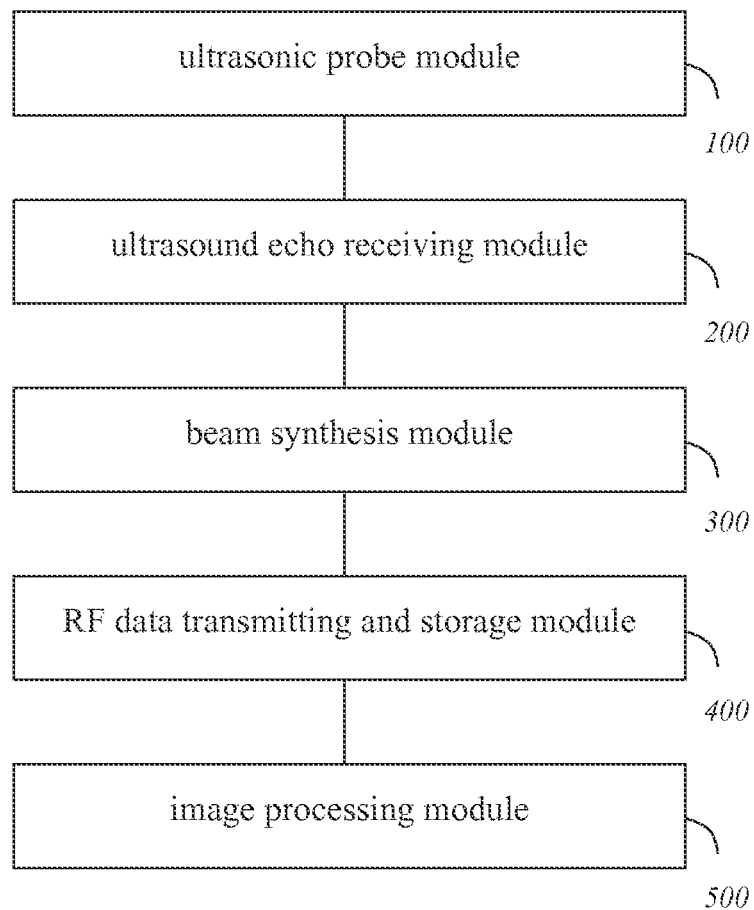
FIG. 4 is a module schematic diagram of an ultrasonic imaging processing system based on RF data in accordance with a first embodiment of the present application.

Comparing with existing technology, the present application, which is based on RF data ultrasound imaging processing, directly conducts ultrasonic imaging based on the obtained RF data of the echo signals in order to obtain the target image. Such method is simple while avoiding loss of data information. Besides, real-time performance and image quality of ultrasonic diagnose appliance using such method are improved, which makes diagnostic information and axial resolution in more detail and clearer, and also lowers the cost of manufacture and usage at the same time. Referring to FIG. 4, FIG. 4 is a module schematic diagram of an ultrasonic imaging processing system based on RF data in accordance with a first embodiment of the present application.

Accordingly, the ultrasonic imaging processing system based on the RF data in accordance with the first embodiment of the present application includes an ultrasonic probe module 100 for sending and receiving ultrasound signal; an ultrasound echo receiving module 200 for receiving echo signals obtained by sending the ultrasound signal; a beam synthesis module 300 for beamforming the echo signals; a RF data transmitting and storage module 400 for getting the RF data from the echo signals; and an image processing module 500 for directly conducting ultrasonic imaging based on the obtained RF data in order to obtain the target image.

Based on the obtained RF data, the image processing module 500 is also used to directly obtain the target image by adopting B mode processing, CF mode processing, PW mode processing and EI mode processing.

Specifically, in an embodiment of the present application, the image processing module 500 adopts the B mode processing to obtain the target image. The image processing module 500 is used for gray map imaging based on the obtained RF data. Accordingly, there are two ways which can be used to obtain the target image by adopting the B mode processing.

In a first way, assuming the RF signal data output by the beam synthesis is I, the absolute value of the RF signal data |I| is used for gray map imaging.

In a second way: assuming the RF signal data output by the beam synthesis is I and then constructing I' using the following formulas:

$I = A \times \cos \omega t,$ $I' = A \times \cos(\omega t + \phi).$

Then, we can achieve the following formulas:

$$\begin{cases} I + I' = 2A\cos\left(\omega t + \frac{\phi}{2}\right)\cos\left(\frac{\phi}{2}\right) \\ I - I' = 2A\sin\left(\omega t + \frac{\phi}{2}\right)\sin\left(\frac{\phi}{2}\right) \end{cases}$$

And then, we can achieve the following formula from the above one:

$$tg\left(\omega t + \frac{\phi}{2}\right) = \frac{I - I'}{I + I'} ctg\left(\frac{\phi}{2}\right),$$

In combination with the formula:

$$tg\left(\omega t + \frac{\phi}{2}\right) = \frac{tg(\omega t) + tg\left(\frac{\phi}{2}\right)}{1 - tg(\omega t)tg\left(\frac{\phi}{2}\right)},$$

we can achieve $tg(\omega t)$. Under this condition, the mode |A| of the RF signal data will be used for gray map imaging using the following formula:

$|A| = |I/\cos \omega t|.$

Accordingly, in an embodiment of the present application, the image processing module 500 adopts the CF mode processing to obtain the target image. The image processing module 500 is specifically applied by adopting Butterfly-Search algorithm or CrossCorrelation algorithm to directly conduct ultrasonic imaging based on the obtained RF data in order to obtain the target image.

In detail, the ButterflySearch algorithm of the CF mode processing is by searching along dimensions of depth and time of the objective reflection ultrasonic signals. The slope of butter line with maximum matching rate is corresponding to the target axial movement speed.

The CrossCorrelation algorithm applied in the CF mode processing is achieved by cross-correlation operating the objective reflection ultrasonic signals along a depth direction. The peak position of the cross-correlation coefficient is corresponding to shift caused by movement. Then the target axial movement speed can be calculated. This algorithm is mainly based on the signal time shift generated by the target movement. In actual calculation, a cross-correlation operation will be done between two adjacent RF data within a sampling volume in order to calculate a speed, and then the total calculated speeds are averaged to get a final speed for the sampling volume.

Accordingly, in an embodiment of the present application, the image processing module 500 adopts the CF mode processing to obtain the target image. The image processing module 500 is specifically applied by adopting an improved CrossCorrelation algorithm to directly conduct ultrasonic imaging based on the obtained RF data in order to obtain the target image.

In detail, traditional CrossCorrelation algorithm can only obtain time shift with integer times of sampling interval, which requires interpolation in order to achieve the precise shift. There are two kinds of interpolation methods. The first method is to interpolation on RF signal in order to upsampling. But it cannot meet the real-time requirement because of high computation complexity. The second method is parabolic, sine or cosine interpolation on crosscorrelation coefficient. Although this method can meet real-time requirements, it is necessary to ensure that true cross-correlation peak is indeed contained in the interpolation curve, which is easily matched the wrong peak.

In an embodiment of the present application, if the image processing module 500 adopts the CrossCorrelation algorithm to directly conduct ultrasonic imaging based on the obtained RF data in order to obtain the target image, based on the conventional CrossCorrelation algorithm, a limited searching scope will be defined through prior value in order to avoid matching error peak cross-correlation coefficient. This will simplify the computation complexity of CrossCorrelation algorithm, and facilitate meeting the real-time requirements.

In detail, time shift (or displacement) of traditional RF signal is continuous along the axial direction and the lateral direction. So, prior value is calculated as the shift of previous point which is in line with the current point, or the shift of same location of an adjacent line corresponding to the current point. For example, if the shift of previous point in the same line is 2, then the shift of the current point is around 2, and cross-correlation search scope can be set between [1, 3].

Accordingly, in an embodiment of the present application, if the image processing module 500 adopts the CrossCorrelation algorithm to directly conduct ultrasonic imaging based on the obtained RF data in order to obtain the target image, it is also feasible to combine the CrossCorrelation algorithm with AutoCorrelation algorithm to directly conduct ultrasonic imaging based on the obtained RF data in order to obtain the target image.

In detail, firstly, the image processing module 500 adopts the CrossCorrelation algorithm to calculate a rough shift value based on which the RF signal can be intercepted. Then, a precise shift value can be calculated by using the AutoCorrelation algorithm. The final accurate shift value can be achieved by adding these two shift value.

Accordingly, in combination with the above description, before the image processing module 500 adopts the Cross-Correlation algorithm, by limiting the cross-correlation search scope through prior values, the shift value of previous point or adjacent point can be directly used as rough shift value of current point. Then, the AutoCorrelation algorithm is used to calculate a precise shift value. By using this method, it is possible to reduce the calculation complexity of the CrossCorrelation algorithm, and avoid aliasing of precise shift value calculated by AutoCorrelation algorithm.

In the process of calculating the precise shift value by using the AutoCorrelation algorithm, it only needs temporarily Hilbert demodulation of the RF signal. Such process can be implemented at the algorithm layer, which simplify the system structure, avoiding data loss.

Accordingly, in an embodiment of the present application, the image processing module 500 adopting PW mode processing to obtain the target image includes adopting a ButterflySearch algorithm or CrossCorrelation algorithm directly conducting ultrasonic imaging based on the obtained RF data in order to obtain the target image.

The ButterflySearch algorithm for achieving the target image of the PW mode processing is to obtain data of each rate component along a depth direction of the RF signal in the sampling box and also along a slope of the velocity. The size of the corresponding data is then calculated for spectrum display.

Referring to FIGS. 6 and 7, in an embodiment of the present application, when the method adopts EI mode processing to achieve target image, the RF data transmitting and storage module 400 is used to get ultrasonic RF signals of the same scan sample in different scan time. The ultrasonic RF signals include a reference signal $S_r$ and a delay signal $S_d$.

In the current embodiment, the ultrasonic RF signals are RF data.

The image processing module 500 is applied to select a section containing the current position of the reference signal $S_r$ and the delay signal $S_d$ via CrossCorrelation operation in order to obtain an integer multiple initial delay of the current location sampling period.

It is understandable that, for easy calculation and low amount of calculation, the image processing module 500 usually selects a section containing the current position of the reference signal $S_r$ and the delay signal $S_d$ for Cross-Correlation operation. Besides, in an embodiment of the present application, the selected section could be a signal having the current position as its center, which will not be described in detail herein.

In the present embodiment, after the image processing module 500 conducting the CrossCorrelation operation regarding the section containing the current position of the reference signal $S_r$ and the delay signal $S_d$, the CrossCorrelation function will be expressed as follows:

$$R_{cc}(m, n, d) = \sum_{m'=-M}^{M} \sum_{n'=-N}^{N} S_r(m+m', n+n') S_d(m+m'+d, n+n')$$

Wherein, m represents signal axis location, n represents signal horizontal location. Value range of m' is between −M to M. Value range of n' is between −N to N. The range between −M and M represents 2M plus one points with the point (m, n) as a center, along the axis direction. The range between −N and N represents 2N plus one point with the point (m, n) as a center, along the horizontal direction. That is to say, the mutual window of the location (m, n) is [2M+1, 2N+1]. Wherein, d represents signal axial relative shift. $R_{cc}$(m, n, d) represents a CrossCorrelation coefficient, when the signal is located at the location (m, n) and the axial relative shift is d. If the maximum search range d belongs to [−D, D], after calculating all the CrossCorrelation coefficients of the range, assuming the maximum location of the CrossCorrelation coefficient is $d_0$, the $d_0 T_s$ is exactly the integer multiple initial delay of the current location sampling period.

In an embodiment of the present application, the method for the image processing module 500 to obtain integer multiple initial delay of the current location sampling period can also be applied to obtain integer multiple initial delay of the current location sampling period of adjacent locations, which will not be depicted in detail herein.

Normally, the CrossCorrelation operation only provides integer multiple initial delay of the current location sampling period and does not accompany the entire process. In order to avoid strange value of the integer multiple initial delay of the current location sampling period, the image processing module 500 usually conducts CrossCorrelation operation applied to multiple adjacent locations in order to get integer multiple initial delay of the current location sampling period of the adjacent locations. Then, a filtering processing will be employed regarding the obtained multiple initial delay in order to obtain a middle value as the initial time delay of the current location.

Further, in the present embodiment, the image processing module 500 conducts Hilbert transformation of the reference signal $S_r$ and the delay signal $S_d$ respectively in order to achieve multiple domain analytic signal.

In the present embodiment, using the $CS_r$ and $CS_d$ to represent the multiple domain analytic signals obtained by Hilbert transformation of the reference signal $S_r$ and the delay signal $S_d$, respectively, the AutoCorrelation function will be expressed as follows:

$$R_{ac}(m, n, d) = \sum_{m'=-M}^{M} \sum_{n'=-N}^{N} CS_r(m+m', n+n') CS_d^*(m+m'+d, n+n')$$

Wherein, symbol * represents conjugate, m represents signal axis location, n represents signal horizontal location. Value range of m' is between −M to M. Value range of n' is between −N to N. The range between −M and M represents 2M plus one points with the point (m, n) as a center, along the axis direction. The range between −N and N represents 2N plus one point with the point (m, n) as a center, along the horizontal direction. That is to say, the mutual window of the location (m, n) is [2M+1, 2N+1]. Wherein, d represents signal axial relative shift. $R_{ac}$(m, n, d) represents a AutoCorrelation coefficient, when the signal is located at the location (m, n) and the axial relative shift is d.

Since the center frequency of the ultrasonic signals is slowly changing with depth going deeply, phase of partial signal keeps linearity.

Further, in the present embodiment, the image processing module 500 conducts AutoCorrelation operation of the multiple domain analytic signal of the present location based on a relative shift between the initial time delay and a second initial time delay in order to achieve the AutoCorrelation coefficient of at least two adjacent points. The second initial time delay is a time delay which has an adjacent value of the initial time delay, and is achieved by retaking an integer multiple sampling cycle with respect to the initial time delay.

Considered the continuity in space of the ultrasound signal delay, each calculated output time delay of the current location can be used as an initial time delay of a next location (axial) or an adjacent location (horizontal). As a result, follow-up calculation process does not need relying on the mutual related exhaustive search. It is only needed to calculate the AutoCorrelation coefficients of at least two points with respect to the initial time delay, which greatly reduces calculation load.

In the above example, the initial time delay of the determined location (m, n) is $d_0 T_s$. In the present embodiment, AutoCorrelation coefficients of the relative shift $d_0$ and at least two adjacent points will be calculated. Take three points for example, AutoCorrelation coefficients will be calculated in turn and obtained as [R(m,n,$d_0$−1), R(m,n,$d_0$), R(m,n,$d_0$+1)].

Further, in the present embodiment, the image processing module 500 is used to achieve a phase based on the AutoCorrelation coefficients of at least two adjacent points, and a fine time delay by using zero-phase linear fitting method.

In an embodiment of the present application, referring to FIGS. 8A and 8B, the difference between the initial time delay and the actual time delay is less than one sampling period according to the zero-phase linear fitting shown in FIG. 8A. The difference between the initial time delay and the actual time delay is greater than one sampling period according to the zero-phase linear fitting shown in FIG. 8B.

Accordingly, the phase obtained by the image processing module 500 based on the AutoCorrelation coefficients of at least two adjacent points and the fine time delay obtained by using zero-phase linear fitting method specifically include calculating each phase according to the AutoCorrelation coefficients of at least two adjacent points; getting slope and intercept of the phases of the obtained at least two points by linear fitting operations; and taking the time delay corresponding to the fitted linear zero phase according to the calculated slope and the calculated intercept as the fine time delay.

Zero-phase linear fit facilitates ensuring the accuracy of the sub sample delay so that the final time delay estimation precision is good. Specifically, based on phase linear characteristics of partial signal, the image processing module 500 conducts linear fit of the above AutoCorrelation coefficients in order to obtain line y=kx+b. Wherein k represents the slope, b represents the intercept, the symbol < represents achieving phase angle which means <(x+jy)=arctan (y/x). As a result, the intersection of the line and the X axis represents the zero phase location, and the time delay corresponds to the intersection is $$-\frac{b}{kT_s}.$$

Further, the fine time delay is actually the time delay $$-\frac{b}{kT_s}.$$

Further, in the present embodiment, the image processing module 500 is also used for adding the obtained initial time delay and the obtained fine time delay in order to get a high precision output delay of the current location.

According to the above example, the high precision output delay of the current location is $$-\frac{b}{kT_s+d_0T_s}.$$

It is understandable that in the present application, it is possible to use a least square method as a linear fit method, which will not be detailed herein.

Further, under normal circumstances, it is necessary to calculate time delays of all locations of a frame signal in an ultrasound scanning process. The frame signal usually includes multiple signals each of which includes time delays corresponding to multiple locations at different depths.

Further, the image processing module 500 takes integer value of the sampling period as an initial time delay of the next location based on the high precision output delay of the current location, and then calculating the time delay of the high precision output delay of the next location using the above method. The next location is a location corresponding to a next depth of a signal which is in the same column of the current signal, or the same depth of a signal of an adjacent column of the current signal.

Referring to FIG. 9, in an embodiment of the present application, the initial time delay of all locations of the column signal is obtained through CrossCorrelation operation. In order to remove strange values, further in adopting EI mode processing to obtain the target image, the image processing module 500 conducts a middle value filtering processing to treat the initial time delay of all locations of the column signal. Then, high precision output delay of all the locations of the column signal will be calculated and obtained. As shown by the arrows of FIG. 9, the high precision output delay of the current location will be used as an initial time delay of a corresponding location of an adjacent signal. Following this rule in turn, calculations will be completed until both the left and the right reach the boundary.

Further, the image processing module 500 is further used to integrate the high precision output delays of all the locations of the obtained frame signal in order to form an image or achieve a new image based on the image in subsequent processing.

In a word, when the image processing module 500 adopts the B mode proceeding, the CF mode proceeding, the PW proceeding and the EI mode processing to obtain the target image, in the process of directly calculating and searching the RF data, it directly conducts ultrasonic imaging based on the obtained RF data in order to obtain the target image. Comparing with existing technology, the present application obtains I/Q orthogonal signal based on the processing of the RF data, and obtains the target image based on the I/Q orthogonal signal via ultrasound imaging processing. The sampling data obtained in such process is more accurate and the calculation result is more accurate as well. Besides, when using the EI mode processing to obtain target image, the EI mode has the advantages of low calculation load and excellent robustness capability, which has very high utility value.

Figure 5:
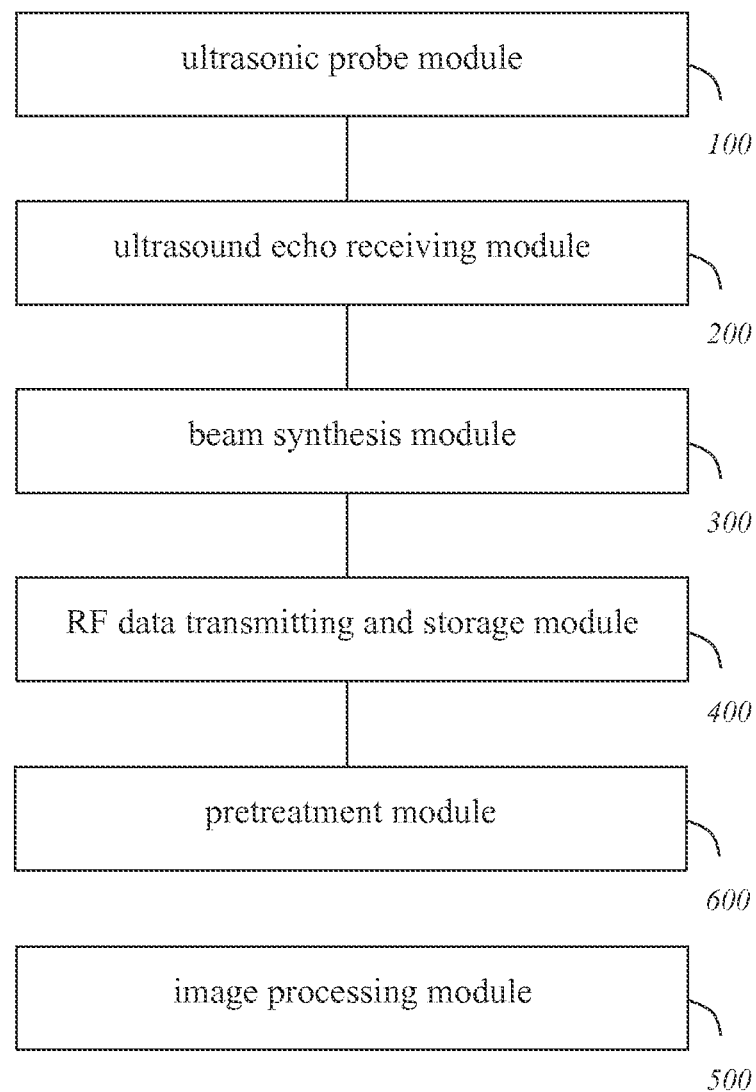
FIG. 5 is a module schematic diagram of an ultrasonic imaging processing system based on RF data in accordance with a second embodiment of the present application.

Referring to FIG. 5, FIG. 5 shows a module schematic diagram of an ultrasonic imaging processing system based on RF data in accordance with a second embodiment of the present application. In order that the target image obtained based on the RF data becomes clearer, the ultrasound imaging processing system based on the RF data shown in FIG. 5 adds a pretreatment module 600 based on the first embodiment shown in FIG. 4. The pretreatment module 600 is applied to pretreat the obtained RF data and remove the system noise of the RF data in order to eventually get a clearer and smoother target image.

Accordingly, there are a lot of ways for the pretreatment module 600 to pretreat the acquired RF data and remove the system noise in the RF data. In an embodiment of the present application, the following method is adopted by the pretreatment module 600 for removing the system noise in the RF data.

Accordingly, noise RF signal data $I_0$ is removed when the collection system is under a silent status. By assuming that the RF signal data of the ultrasonic echo in practical application is I, it is possible for the pretreatment module 600 to remove the background noise by using I minus $I_0$.

According to the above description, the ultrasonic imaging processing method and system based on RF data according to the present application are also called RF data platform technology. It is possible to directly conduct ultrasonic imaging treatment based on the obtained RF data of the echo signals in order to obtain the target image. An embodiment of the ultrasonic imaging processing system based on RF data according to the present application is simple and avoids loss of data information. Besides, real-time performance and image quality of ultrasonic diagnose appliance by using such method and system are improved, which makes diagnostic information and axial resolution in more detail and clearer, and also lowers the cost of manufacture and usage at the same time.

In describing the above system, for convenient description, the system is divided into various modules with different functionality. Of course, in implementing the present application, it is feasible to realize the functions of all the modules within one or more software and/or hardware.

It is understandable according to the above description that those of ordinary skill in the art can clearly understand the present application can be realized by software and required universal hardware platform. Based on such understanding, the essential technical solution of the present application or the part makes contribution to the existing technology can be expressed through software products. The software products can be saved in media, such as ROM/RAM, disk, and CD etc. Besides, it also possible to use a computer equipment (such as a PC, or an information exchange server, or a network equipment) to executive the method of each embodiment or some parts of the embodiments of the present application.

The embodiments of the system described above are only schematic, in which the modules described separately may be or may not be physically separated. The parts for module display may be or may not be a physical module, which means they can be located in one place or distributed in multiple network modules. It is possible to select part or all modules to realize the purpose of the present application, which is feasible for those of ordinary skill in the art to understand and implement after reviewing the present application.

It is to be understood, however, that even though exemplary embodiments have been set out in the foregoing description, it does not mean that each embodiment has only one independent technical solution. The narration of the specification is only for clear description. Those of ordinary skill in the art should consider the specification as a whole. Technical solutions of all the embodiments can be appropriately combined to form other embodiments which are understandable by those skilled in the art.

What is claimed is:

1. An ultrasonic imaging processing method:
    S1, receiving echo signals which are obtained by sending ultrasound signals;
    S2, beamforming the echo signals;
    S3, obtaining beamformed radio frequency (RF) data based on the beamformed echo signals; and
    S4, conducting an ultrasonic imaging process based on the obtained beamformed RF data in order to obtain a target image, the ultrasonic imaging process including selecting elastography (EI) mode processing based on the obtained beamformed RF data in order to obtain the target image, wherein the EI mode processing to obtain the target image comprises:
        adopting the beamformed RF data based on scans of a same sample at two different times, the beamformed RF data comprising a reference signal $S_r$ and a delay signal $S_d$;
        selecting a segment containing a current signal processing location in the reference signal $S_r$ and in the delay signal $S_d$ for CrossCorrelation operation in order to obtain an initial time delay of the current signal processing location, wherein the initial time delay is a first integer multiple of a sampling period;
        conducting Hilbert transformation of the reference signal $S_r$ and the delay signal $S_d$, respectively, in order to achieve multiple domain analytic signals;
        respectively conducting an AutoCorrelation operation of the multiple domain analytic signals of the current signal processing location in order to obtain AutoCorrelation coefficients of at least two adjacent points based on a relative shift of the initial time delay and a second initial time delay;
        obtaining a second time delay using linear fitting based on phases of the at least two adjacent points, the phases being based on the AutoCorrelation coefficients of the at least two adjacent points and the second time delay corresponding to a zero phase on a line of the linear fitting; and
        adding the obtained initial time delay and the obtained second time delay in order to get an output delay of the current signal processing location, wherein
        a frame of the echo signals comprises columns of signals over a same area at different depths, each column of which comprises time delay estimations of multiple locations at different depths;
        the EI mode processing to obtain the target image comprises taking a second integer multiple of the sampling period of the current signal processing location as an initial time delay of a next location based on the output delay of the current signal processing location, and then calculating an output delay of the next location; and
        the next location is a location corresponding to a next depth to which a signal in a same column of a current signal of the echo signals is directed, or a same depth to which a signal in an adjacent column of the current signal is directed.

2. The ultrasonic imaging processing method as claimed in claim 1, wherein the step S3 comprises:
    pretreating the beamformed RF data and removing system noise of the beamformed RF data.

3. The ultrasonic imaging processing method as claimed in claim 1, wherein the step S1 further comprises obtaining a frame of the echo signals and wherein the EI mode processing to obtain the target image comprises integrating the output delay of the current signal processing location and the next location of the obtained frame of the echo signals in order to form the target image.

4. The ultrasonic imaging processing method as claimed in claim 1, wherein selecting the segment containing the current signal processing location in the reference signal $S_r$ and the delay signal $S_d$ for CrossCorrelation operation in order to obtain the initial delay comprises:
    obtaining integer multiples of multiple sampling periods according to multiple locations adjacent to the current signal processing location;
    conducting median filtering of the obtained integer multiples of multiple sampling periods; and taking an obtained median as the initial time delay of the current signal processing location.

5. The ultrasonic imaging processing method as claimed in claim 1, wherein obtaining the second time delay comprises:
    respectively calculating phases of the at least two adjacent points according to the AutoCorrelation coefficients of the at least two adjacent points;
    obtaining slope and intercept of the phases of the obtained at least two adjacent points using the linear fitting; and
    selecting a time delay corresponding to the zero phase on the line of the linear fitting as the second time delay.

6. An ultrasonic imaging processing system the system, comprising:
    an ultrasonic probe, which, in operation, sends ultrasound signals;
    an ultrasound echo receiver, which, in operation, receives echo signals which are obtained by sending the ultrasound signals;
    a beam synthesizer, which, in operation, beamforms the echo signals;
    data processing circuitry, which, in operation, obtains the beamformed radio frequency (RF) data based on the beamformed echo signals;
    image processing circuitry, which, in operation, conducts an ultrasonic imaging process based on the obtained beamformed RF data in order to obtain a target image, wherein based on the obtained beamformed RF data, the image processing circuitry, in operation, selects elastography (EI) mode processing in order to obtain the target image, wherein the beamformed RF data is obtained based on scans of a same sample at two different times, the beamformed RF data comprising a reference signal $S_r$ and a delay signal $S_d$; and
    the image processing circuitry, in operation:
        selects a segment containing a current signal processing location in the reference signal $S_r$ and in the delay signal $S_d$ for CrossCorrelation operation in order to obtain an initial time delay of the current signal processing location, wherein the initial time delay is a first integer multiple of a sampling period;

conducts Hilbert transformation of the reference signal $S_r$ and the delay signal $S_d$, respectively, in order to achieve multiple domain analytic signals;

respectively conducts an AutoCorrelation operation of the multiple domain analytic signals of the current signal processing location in order to obtain AutoCorrelation coefficients of at least two adjacent points based on a relative shift of the initial time delay and a second initial time delay;

obtains a second time delay using linear fitting based on phases of the at least two adjacent points, the phases being based on the AutoCorrelation coefficients of the at least two adjacent points and the second time delay corresponding to a zero phase on a line of the linear fitting; and adds the obtained initial time delay and the obtained second time delay in order to get an output delay of the current signal processing location, wherein a frame of the echo signals comprises columns of signals over a same area at different depths, each column of which comprises time delay estimation of multiple locations at different depths;

the image processing circuitry, in operation, uses a second integer multiple of the sampling period of the current signal processing location as an initial time delay of a next location based on the output delay of the current signal processing location, and then calculates an output delay of the next location; and the next location is a location corresponding to a next depth to which a signal in a same column of a current signal of the echo signals is directed, or a same depth to which a signal in an adjacent column of the current signal is directed.

7. The ultrasonic imaging processing system of claim 6, comprising pretreatment circuitry, which, in operation, pretreats the beamformed RF data and removes system noise of the beamformed RF data.

8. The ultrasonic imaging processing system of claim 6, wherein the ultrasound echo receiver obtains a frame of the echo signals and wherein the image processing circuitry, in operation, integrates the output delay of the current signal processing location and the next location of the obtained frame of the current signal in order to form the target image.

9. The ultrasonic imaging processing system of claim 6, wherein the image processing circuitry, in operation:

obtains integer multiples of multiple sampling periods according to multiple locations adjacent to the current signal processing location;

conducts median filtering of the obtained integer multiples of multiple sampling periods; and takes an obtained median as the initial time delay of the current signal processing location.

10. The ultrasonic imaging processing system of claim 6, wherein the image processing circuitry, in operation:

calculates respective phases of the at least two adjacent points according to the AutoCorrelation coefficients of the at least two adjacent points;

obtains a slope and intercept of the phases of the obtained at least two adjacent points using the linear fitting; and selects a time delay corresponding to a zero phase on the line of the linear fitting as the second time delay.

* * * * *